United States Patent [19]

Nelson et al.

[11] Patent Number: 5,776,087
[45] Date of Patent: Jul. 7, 1998

[54] BACK BRACE

[75] Inventors: Ronald E. Nelson, Chetek, Wis.;
Stefan Lüssenhop, Uetersen, Germany

[73] Assignee: Tamarack International, Inc., Chetek, Wis.

[21] Appl. No.: 694,488

[22] Filed: Aug. 7, 1996

[51] Int. Cl.⁶ ............................................. A61F 5/00
[52] U.S. Cl. ...................................... 602/19; 2/255
[58] Field of Search ........................ 602/19; 128/96.1, 128/99.1, 101.1, 112.1, 115.1; 2/311, 312, 321, 255

[56]       References Cited

U.S. PATENT DOCUMENTS

| 3,927,665 | 12/1975 | Wax | 602/19 |
| 4,245,628 | 1/1981 | Eichler | 602/19 |
| 5,257,419 | 11/1993 | Alexander | 602/19 X |
| 5,399,151 | 3/1995 | Smith | 602/19 |
| 5,499,965 | 3/1996 | Sanchez | 602/19 |
| 5,503,620 | 4/1996 | Danzger | 602/19 |
| 5,533,961 | 7/1996 | Iwata | 602/19 |
| 5,548,843 | 8/1996 | Chase et al. | 602/19 X |

*Primary Examiner*—Linda C. Dvorak
*Attorney, Agent, or Firm*—Nawrocki, Rooney & Sivertson, P.A.

[57]        ABSTRACT

A back brace having an at least partially elastic waist belt, a substantially non-elastic rear waist belt portion and a pair of arms extending from the rear portion and having overlapping interconnecting end portions for holding the belt in place around the waist of a human body. Each of the arms carries a pocket, and each of the pockets is adapted to carry a stiff, flexible stay. A pair of non-elastic shoulder straps each have one end anchored by the rear member of the back brace or belt and another end adjustably anchored by a strap connector which is in turn connected to a non-elastic strap support mounted on each arm. Each of the pockets and its related insert have a curved upper portion specifically designed to adapt to the curvature of the lower rib of the body.

8 Claims, 4 Drawing Sheets

BACK BRACE

BACKGROUND OF THE INVENTION

The present invention relates generally to orthopedic devices, more particularly to body braces and supports, and still more particularly to back braces.

DESCRIPTION OF THE PRIOR ART

The use of flexible back braces for restorative support and/or prevention of injury is well known.

In the prior art, back braces take a number of known forms or constructions. In the prior art believed closest to the apparatus of this invention, it is known to use a wide, flexible and elastic waist belt or band. The waist belt may have a stiff or less flexible rear or posterior portion adapted to be placed adjacent the lumbosacral area of the body, and a pair of arms extending from the stiffened rear area. At least a portion of each of the arms is stretchable or elastic with connectors positioned at the ends of the arms to fasten the belt in place. Hook and loop fastener materials may be used to provide a multiple number of positions for connection of the arms to thus allow a stretching around various sizes of the human body.

Such prior art back braces are often fitted with a pair of suspenders or shoulder straps of an elastic material, which serve the purpose of helping to hold the back brace in position on the body—including when the frontal portion of the brace is loosened, but it is desired to hold the brace in position for future use.

In the known back braces of the type described above, there is little or no structure which will prevent a relative rotation between the shoulders of the human body and the pelvis, which rotation has been found to be undesirable, particularly in the case of lifting heavy objects. In addition, the prior art flexible, elastic waist belts have an undesirable roll-over (curving of the belt) tendency and lack structure to prevent the body from bending within the belt.

SUMMARY OF THE INVENTION

The present invention provides a unique structure designed to address the above-described tendencies of the prior art. More specifically, a preferred apparatus in accordance with this invention provides that the suspenders or shoulder straps of the present invention be non-elastic and have one end rigidly connected to the rear portion of the brace and another end adjustably connected to a non-elastic portion on each arm or side of the brace or waist belt. The adjustable connection, when the waist belt is in place, will lie between the lumbosacral area and the crest of the ilium on each side of the body. This use of a non-elastic suspender has the effect of locking the shoulders over the pelvis in a manner to inhibit relative rotation between the body's shoulders and pelvis when the brace is in use.

Other structures in accordance with the present invention include a pair of pockets, one on each arm of the waist belt, and a stiff, flexible insert for each of the pockets, which serve the function of inhibiting the curling or rolling of the belt, as well as inhibiting the body's bending within the belt. Both the pocket and the insert of the present invention have upper portions which are curved to approximate the arch or curve of the lower ribs of the body as the belt wraps toward the front of the body to thus allow the sides of the brace to lie under the ribs.

BRIEF DESCRIPTION OF THE DRAWINGS

The objects and many of the attendant advantages of the present invention will be readily appreciated as they become better understood by reference to the following detailed description when considered in connection with the accompanying drawings, in which drawings like reference numerals designate like parts throughout the figures thereof, and wherein.

DETAILED DESCRIPTION OF THE PREFERRED EMBODIMENTS

Figure 1:
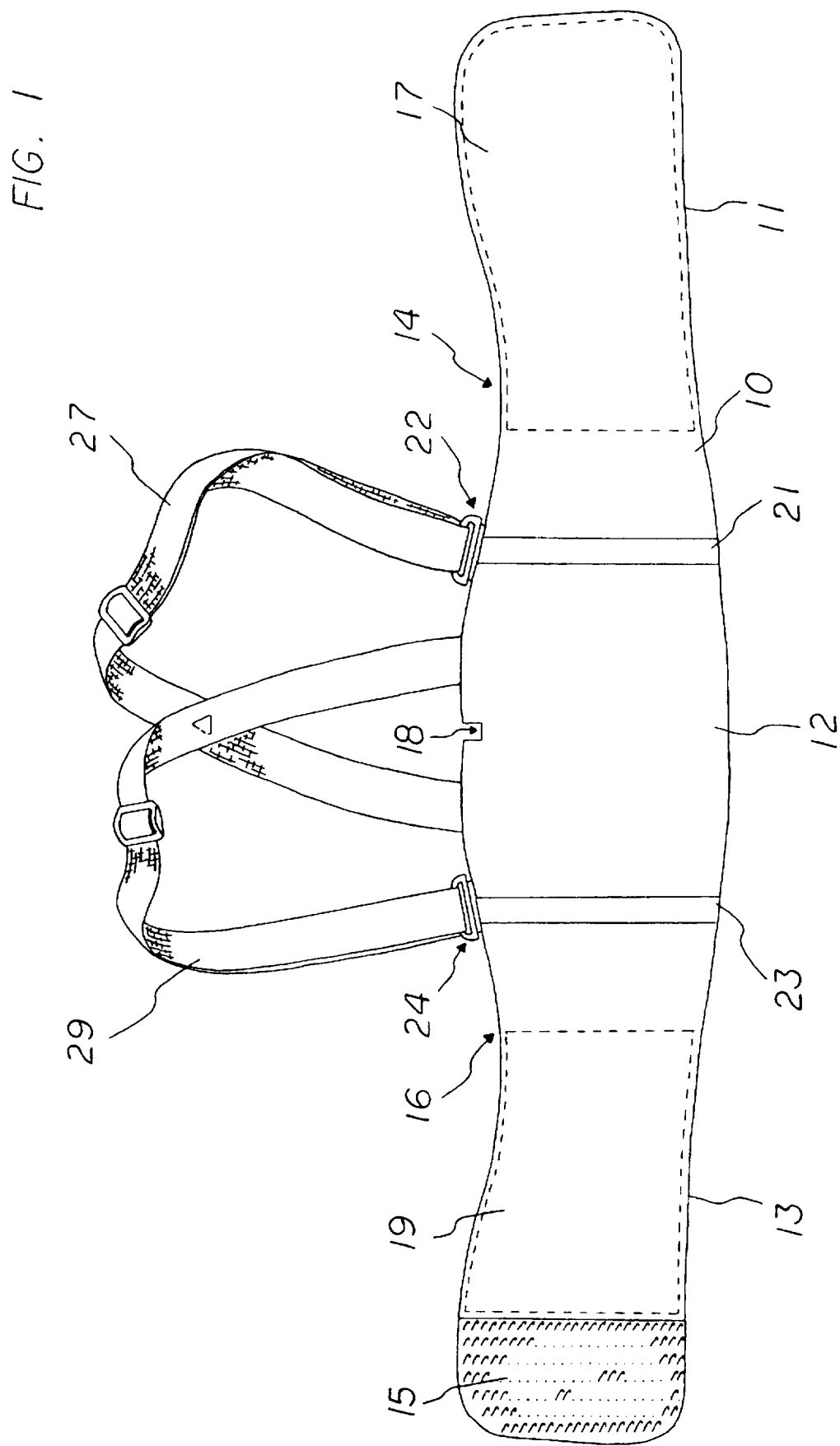
FIG. 1 is a plan view of the inside face of a back brace in accordance with the present invention.

FIG. 1 illustrates a plan view of a back brace in accordance with the present invention including a waist belt indicated generally at 10. Brace or belt 10 includes a pair of flexible arms 11 and 13, each of which includes at least a portion of elastic or stretchable material. Mounted on each of arms 11 and 13 are, respectively, a pocket 17 and a pocket 19 shown by dotted lines. Pockets 17 and 19 are adapted to receive a stiff, flexible stay such as that described in the discussion of FIG. 2 below. The pockets 17 and 19 open toward each other to accept a stay therein and extend from the pocket opening toward the terminal ends of the arms 11 and 13. The pocket openings are positioned to generally overlie the crest of the ilium when the brace is worn.

As can be seen in FIG. 1, the upper portion of arm 11 comprises a curve 14. Curve 14 is designed to lie below the curve of the lower rib of a human body to eliminate or inhibit undesirable chaffing of—or pressure on (and under)—the rib when brace 10 is in place around the waist of a human body. Generally, the curve 14 causes the brace arms to pass below the lower rib as it wraps toward the front of the body. It can also be seen in FIG. 1 that arm 13 includes a curve 16 similar to, and having the same purpose as, curve 14 described above.

Figure 3:
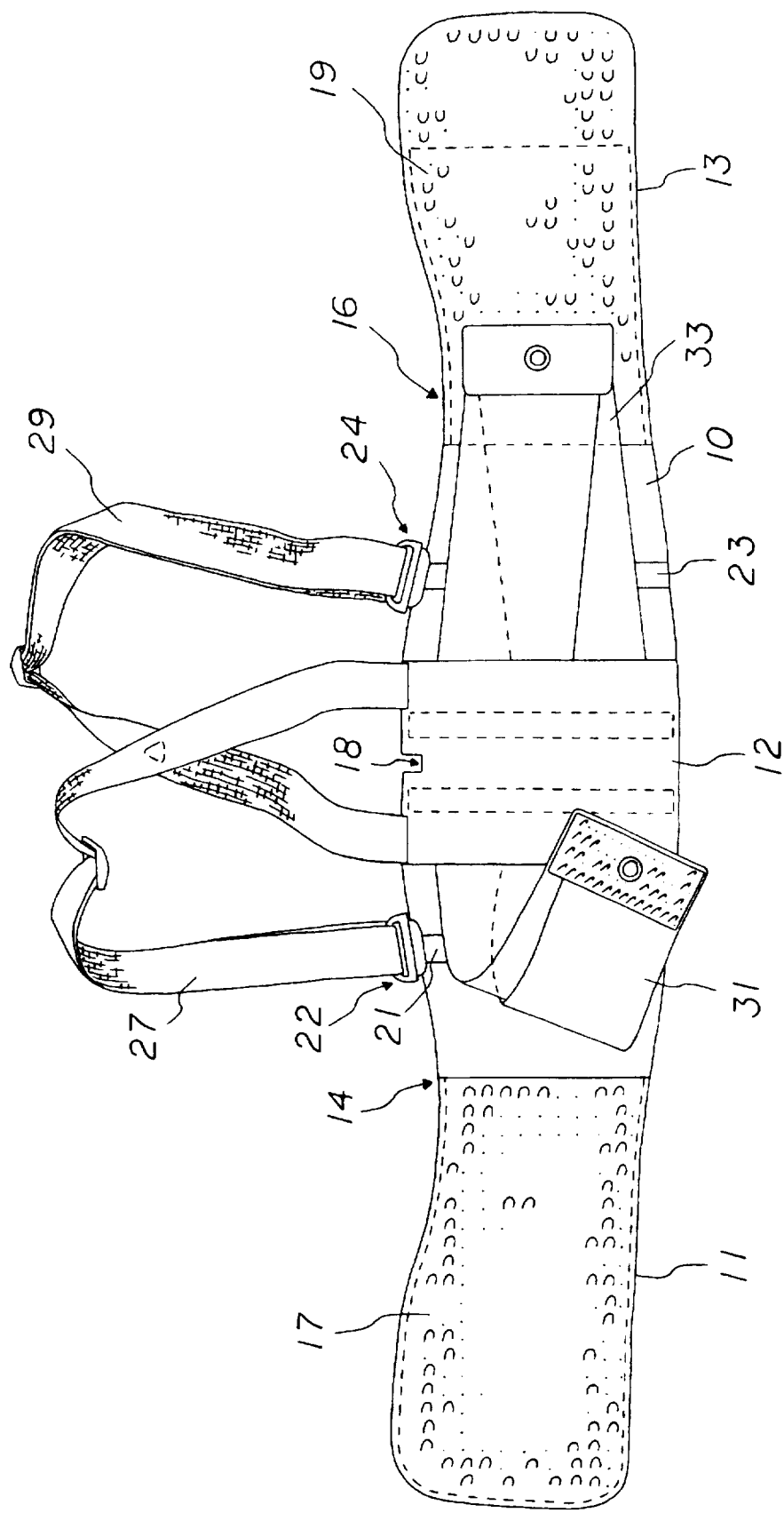
FIG. 3 is a plan view of the outside of the back brace of FIG. 1 and showing the connection of a pair of side pulls on the back brace of this invention.

In FIG. 1, the terminal portion of arm 13 is covered with hook elements 15 of the well-known hook and loop fastener, thus providing a connection means for belt or back brace 10, via a cooperating loop surface on arm 11 (see FIG. 3). The use of such hook and loop fasteners enables a virtually infinite number of connection points along the overlapping end portions of arms 11 and 13, thus enabling the use of one size of back brace for many sizes of bodies and also enabling a variation in the tightness of the belt 10 around the waist of the body.

Further in FIG. 1, a pair of non-elastic strap support or anchor members 21 and 23 are shown mounted on brace or belt 10, each of strap anchors 21 and 23 being spaced from the respective end of the non-elastic rear portion of belt 10, here shown as portion 12. Strap anchor 21 is rigidly connected to a strap connector 22, while strap anchor 23 is rigidly connected to a strap connector 24. Strap anchors 21 and 23 may be formed of strips of generally inelastic material sewn or otherwise attached over the surface (and preferably both the inner and outer surface) of belt 10.

A pair of non-elastic shoulder straps 27 and 29 are shown having one end fixedly or rigidly connected to rear portion or member 12, and another end adapted for adjustable connection, through the respective of strap connectors 22 and 24, to a sliding connector cooperating with the straps 27 and 29, in known manner. The use of these novel non-elastic shoulder straps, rigidly connected to non-elastic rear member 12, provides the desired result of inhibiting rotation of the shoulders of the body with respect to the pelvis. That is, straps 27 and 29 of the present invention, connected in the manner described, have the effect of locking the shoulders over the pelvis. Adjustment of the straps via connectors 22 and 24 and cooperating sliding elements on the belts is well known in the art. The sliding elements may be made in a contrasting color to the color of the straps 27 and 29 to facilitate locating them for adjustment.

Also shown in FIG. 1 is a notch 18 in non-elastic rear member 12. Notch 18 serves the purpose of relieving stress on the upper edge of member 12 from straps 27 and 29 when the brace is worn in the usual manner, and also serves the purpose of relieving the effect of the upper edge of member 12 against the spinal area of the posterior or dorsal portion of the body when brace 10 is worn.

Figure 2:
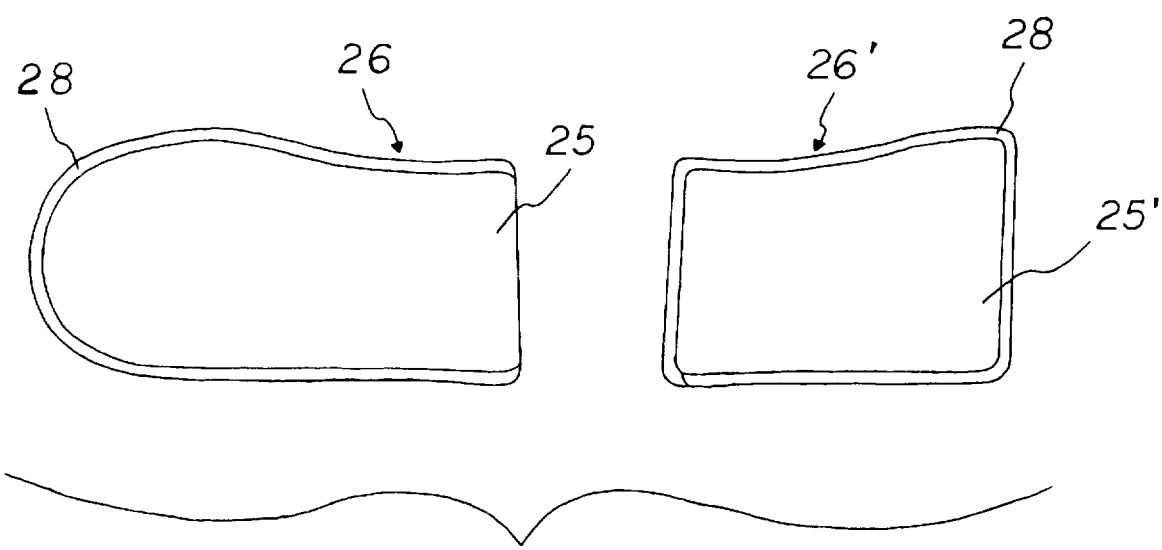
FIG. 2 is a plan view of inserts for the back brace of FIG. 1.

Referring now to FIG. 2 there are shown stays or inserts 25 and 25 designed to fit within the respective pocket 17 and 19 of FIG. 1. As can be seen, stays 25 and 25' have a curve 26 (and 26') in their upper portion, which curve 26/26' is designed to match curves 14 and 16 in pockets 17 and 19 for the purpose of protecting the lower rib of the body, as described. Also shown in FIG. 2 is a material edging 28 around the outer edge of stays 25/25', which material serves the purposes of padding the edges of stays 25/25' and increasing the friction between stays 25/25' and the internal portion of pockets 17 and 19, for the obvious purpose of helping to hold stays 25/25' in position within the respective pocket. Preferably, stays 25 and 25' are a stiff, flexible material which is non-flexible or stiff within its own plane and flexible in a direction outside of its own plane, polyethylene having a thickness of 0.060 inches, for example. The stays 25 and 25' act to prevent curling of the arms 11 and 13 of belt 10 while forcing a correct lifting position when the belt 10 is worn. That is, the stays 25/25' restrict or prevent bending of the body within the brace 10.

Referring now to FIG. 3, there is shown a plan view of the outside of brace or belt 10. As shown in FIG. 3, each of arms 11 and 13 carries an elastic, flexible side pull, 31 and 33, respectively. Side pulls 31 and 33 each have one end connected to non-elastic member 12. The terminal ends of pulls 31 and 33 are designed to overlie and interconnect with their respective arm 11 and 13 at a number of positions in the front of the body. Side pulls 31 and 33 provide additional compression on the lumbosacral area of the body when brace 10 is in use. In the present invention, side pulls 31 and 33 perform the additional function of tightly holding pockets 17 and 19, each containing an insert 25/25', against the sides of the body to assist in the non-curling, non-bending features of the present invention, as described. As can also be seen in FIG. 3, essentially the entire pocket areas 17 and 19 of the outer surface of arms 11 and 13 are provided with loop elements forming a portion of the hook and loop fasteners described. Indeed, the pockets may be formed by securing the edges of a panel of loop material to the edges of the respective arm. The terminal ends of side pulls 31 and 33 may be secured at any point on these loop material panels.

Figure 5:
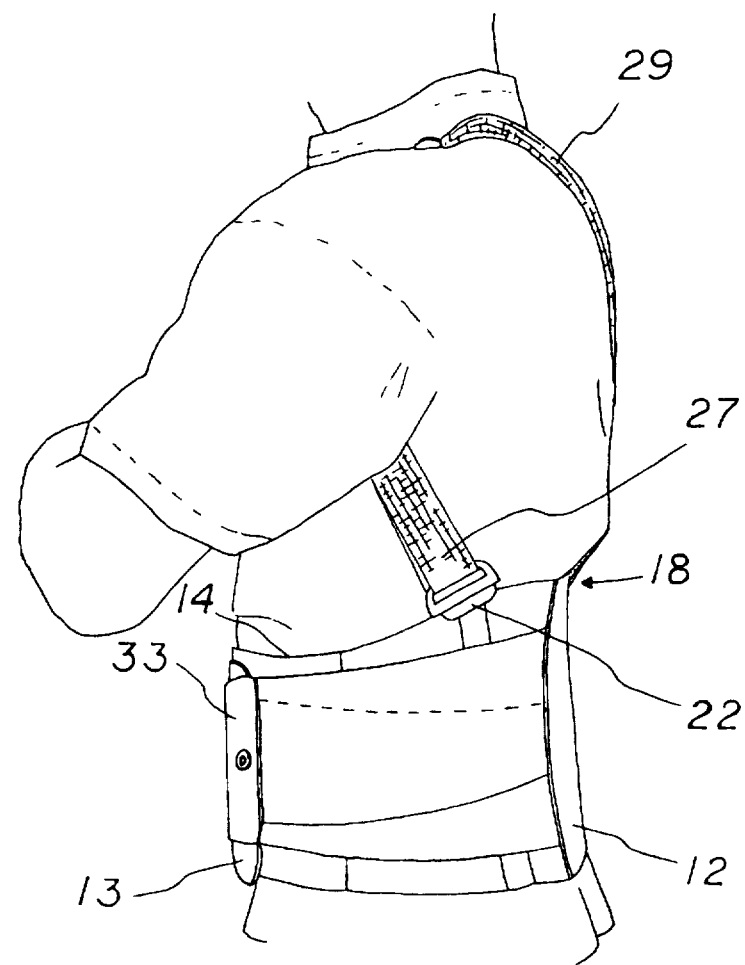
FIGS. 4 and 5 are views of the back brace of FIGS. 1–3 as it appears in use.
Figure 4:
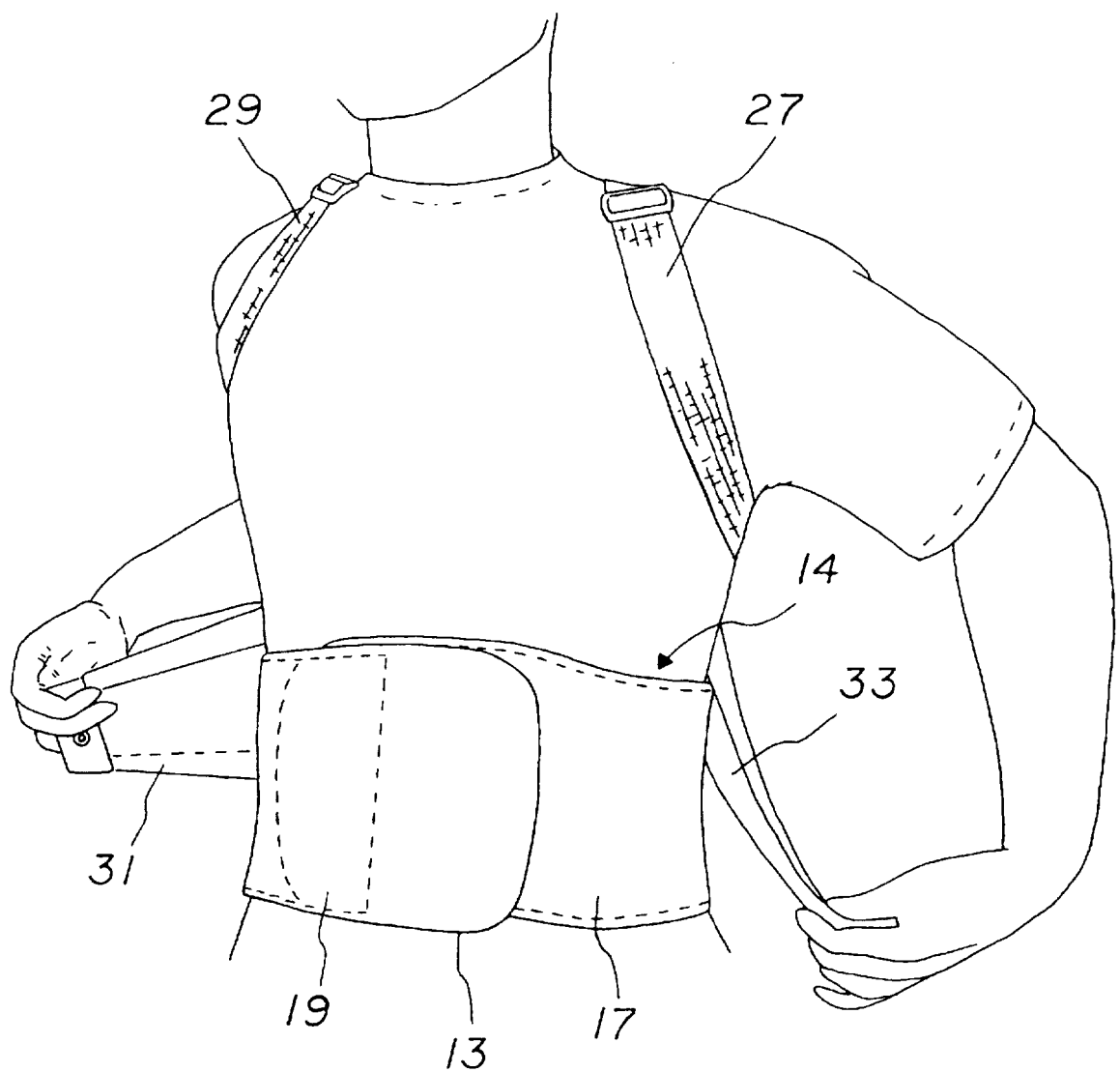

FIGS. 4 and 5 are views of the apparatus of the present invention when in use on the human body. Here it can be seen how non-elastic member 12 fits at the dorsal portion of the body adjacent to the lumbosacral area and how belt 10 with side pulls 33 and 31 encompass the body with the hook elements of the terminal ends of side pulls 31 and 33 secured to the loop panels of arms 11 and 13. Also, it can be seen how each of non-elastic shoulder straps 27 and 29 have one end connected to member 12 and the other end, after passing over a shoulder, adjustably connected to the respective of strap connectors 22 and 24. Of course, one end of the straps 27 and 29 may be anchored to belt 10 in some other manner, as by being fastened to each other and to a third strap to form a "Y", with the third strap being connected to the belt, at member 12, for example. Strap connectors 22 and 24 (and strap anchors 21 and 23) are positioned on brace 10 to lie posterior to the crest of the ilium when the brace is worn. With the non-stretch shoulder straps 27 and 29 taught, this placement of the connectors 22 and 24 locks the shoulders over the pelvis to maintain the thorax, lumbar portion of the spine and the pelvis in alignment. Such alignment reduces the potential for injury during lifting. FIG. 5 in particular illustrates how the curves 14 and 16 underlie the curve or arch of the lower ribs.

Having thus described the preferred embodiments of the present invention, those of skill in the art will readily appreciate the other useful embodiments within the scope of the claims hereto attached.

What is claimed is:

1. Back brace apparatus for a human body comprising:
   a waist belt including a pair of at least partially elastic arms each having an end portion, said arm portions including closure means for interconnection thereof at a plurality of positions;
   a non-elastic stay member connected to said belt at a position adapted to overlie the dorsal area of the body when the belt is worn;
   a non-elastic strap connection element mounted on each of said arms at a position spaced from said support member, and a strap connector mounted on each of said strap connection elements;
   a pair of non-elastic shoulder straps each having a first end anchored to said support member and a second end adjustably connected to different ones of said strap connectors;
   a pocket mounted on each of said arms at a position between the arm ends and the crest of the Ilium when the belt is worn, an upper portion of each of said pockets being curved to underlie the curve of the lower ribs of the body; and
   said stay members being within said pockets, each stay member comprising a material stiff within the plane of said stay member and flexible outside the plane of said stay member, and each of said stay members including an upper portion curved to underlie the curve of the lower ribs of the body.

2. The apparatus of claim 1 in which each of said strap connection elements is mounted on said arms at a position spaced from said stay member toward the crest of the ilium when said belt is worn.

3. The apparatus of claim 1 in which each of said strap connection elements is mounted on said arms at a position spaced from said stay member toward the crest of the ilium when said belt is worn.

4. The apparatus of claim 3 including:
   an elastic side pull member mounted on each of said arms for providing additional compression on the lumbosacral area of the body when said brace is worn, each of said pull members overlying one of said arms and having connection means for securing the pull members to their associated arm.

5. The apparatus of claim 1 including:
   an elastic side pull member mounted on each of said arms for providing additional compression on the lumbosacral area of the body when said brace is worn, each of said pull members overlying one of said arms and having connection means for securing the pull members to their associated arm.

6. A back brace apparatus for a human body having a flexible, at least partially stretchable belt including a non-elastic rear portion and a pair of overlapping, interconnectable arms extending from said rear portion, the improvement comprising:

- a non-elastic strap support portion on each of said arms, each of said support portions spaced from said rear portion and connected to a strap connector;
- a pair of non-stretch, flexible shoulder straps each having a first end rigidly anchored by said rear portion and a second end adjustably connected to one of said strap connectors;
- said non-elastic strap support portions being mounted on said arms in a position posterior to the crest of the Ilium when the brace is worn on the body;
- a socket formed in each of said arms; and
- a stiff flexible stay within each of said pockets, said pockets and said stays each having a curved upper portion adapted to generally underlie the arch of the lower ribs as the arm wraps around the body.

7. A back brace apparatus for a human body having a flexible, at least partially stretchable belt including a non-elastic rear portion and a pair of overlapping, interconnectable arms extending from said rear portion, the improvement comprising:

- a pocket formed in each of said arms; and
- a stiff, flexible stay within each of said pockets, said pockets and said stays each having a curved upper portion adapted to generally underlie the arch of the lower ribs as the arm wraps around the body.

8. The apparatus of claim 7 further comprising a pair of non-stretch shoulder straps having first and second ends anchored by said brace posterior to the crest of the ilium when the brace is worn.

* * * * *